(12) United States Patent
Pacchetti et al.

(10) Patent No.: US 11,590,101 B2
(45) Date of Patent: Feb. 28, 2023

(54) USE OF A COMPOSITION COMPRISING 7-HYDROXYMATAIRESINOL

(71) Applicant: LINNEA S.A., Riazzino (CH)

(72) Inventors: Barbara Pacchetti, Riazzino (CH); Fabio Blandini, Pavia (IT); Francesca Siani, Pavia (IT)

(73) Assignee: LINNEA S.A., Riazzino (CH)

( * ) Notice: Subject to any disclaimer, the term of this patent is extended or adjusted under 35 U.S.C. 154(b) by 147 days.

(21) Appl. No.: 16/611,420

(22) PCT Filed: May 9, 2018

(86) PCT No.: PCT/EP2018/061960
§ 371 (c)(1),
(2) Date: Nov. 6, 2019

(87) PCT Pub. No.: WO2018/206621
PCT Pub. Date: Nov. 15, 2018

(65) Prior Publication Data
US 2020/0170996 A1     Jun. 4, 2020

(30) Foreign Application Priority Data
May 11, 2017 (IT) .................. 102017000050994

(51) Int. Cl.
| | |
|---|---|
| *A61K 31/365* | (2006.01) |
| *A61P 25/28* | (2006.01) |
| *A61P 25/16* | (2006.01) |
| *A23L 33/10* | (2016.01) |

(52) U.S. Cl.
CPC ............ *A61K 31/365* (2013.01); *A23L 33/10* (2016.08); *A61P 25/16* (2018.01); *A61P 25/28* (2018.01)

(58) Field of Classification Search
None
See application file for complete search history.

(56) References Cited

U.S. PATENT DOCUMENTS

| | | | |
|---|---|---|---|
| 6,451,849 B1 | 9/2002 | Ahotupa et al. | |
| 7,008,666 B2 * | 3/2006 | Ahotupa ................ | A61K 31/05 426/648 |
| 2014/0308379 A1 | 10/2014 | Christofidou-Solomidou et al. | |

FOREIGN PATENT DOCUMENTS

| | | |
|---|---|---|
| WO | WO 2006/072647 A1 | 7/2006 |
| WO | WO 2014/083171 A1 | 6/2014 |
| WO | WO 2015/173345 A1 | 11/2015 |

OTHER PUBLICATIONS

Treatment, 2021, https://www.merriam-webster.com/dictionary/treatment.*
Ruggeri et al., Journal of Medicinal Chemistry, 2015, 58, 8513-8528.*
PD-Prevention, 2021, https://my.clevelandclinic.org/health/diseases/8525-parkinsons-disease-an-overview.*
PD-Cure, 2021, https://www.mayoclinic.org/diseases-conditions/parkinsons-disease/diagnosis-treatment/drc-20376062.*
AD, 2021, https://www.mayoclinic.org/diseases-conditions/parkinsons-disease/diagnosis-treatment/drc-20376062.*
Baluchnejadmojarad, T., et al., "Sesamin imparts neuroprotection against intrastriatal 6-hydroxydopamine toxicity by inhibition of astroglial activation, apoptosis, and oxidative stress", Biomedicine & Pharmacotherapy, vol. 88, Apr. 1, 2017, XP055456470, pp. 754-761.
Sutachan, J. J., et al., "Cellular and molecular mechanisms of antioxidants in Parkinson's disease", Nutritional Neuroscience, 2012, vol. 15 No. 3, pp. 120-126.
Aquilano, K., et al., "Role of nitric oxide synthases in Parkinson's disease; a review on the antioxidant and anti-inflammatory activity of polyphenols", Neurochemistry Research, 2008, vol. 33 No. 12, pp. 2416-2426 (with cover page).
Cosentino, M., et al.. Immunomodulatory activity of the lignan 7-hydroxymatairesinol potassium acetate (HMR/lignan™) extracted from the heartwood of Norway spruce (*Picea abies*), International Immunopharmacology, 2010, vol. 10 No. 3, pp. 339-343.
Cosentino M., et al., "Estrogenic activity of 7-hydroxymatairesinol potassium acetate (HMR/lignan™) from Norway spruce (*Picea abies*) knots and of its active metabolite enterolactone in MCF-7 cells", Pharmacological Research, 2007, vol. 56, 140-147.
Spilioti, E., et al., "Lignans 7-hydroxymatairesinol and 7-hydroxymatairesinol 2 exhibit anti-inflammatory activity in human aortic endothelial cells", Mol Nutr. Food Res., 2014, vol. 58, XP55138380, pp. 749-759.
Blandini, F., et al., "Animal models of Parkinson's disease", Federation of European Biochemical Societies Journal, 2012, vol. 279 No. 7, pp. 1156-1166.
Tang, Y., et al., "Differential Roles of M1 and M2 Microglia in Neurodegenerative Diseases", Mol Neurobiol. Mar. 2016; vol. 53 No. 2, pp. 1181-1194. doi:10.1007/s112035014-9070-5. Epub Jan. 20, 2015.

* cited by examiner

*Primary Examiner* — Sun Jae Yoo
(74) *Attorney, Agent, or Firm* — Oblon, McClelland, Maier & Neustadt, L.L.P.

(57) ABSTRACT

7-hydroxymatairesinol and a composition thereof for ameliorating the neurodegenerative disorders, in particular the disorders associated with dopaminergic neurons loss, such as the Parkinson's disease.

3 Claims, 10 Drawing Sheets

USE OF A COMPOSITION COMPRISING 7-HYDROXYMATAIRESINOL

CROSS REFERENCE TO RELATED APPLICATIONS

This application is 371 of International Patent Application No. PCT/EP2018/061960, filed on May 9, 2018, and claims priority to Italian Patent Application No. 102017000050994, filed on May 11, 2017, both of which are incorporated herein by reference in their entireties.

FIELD OF THE INVENTION

The present invention relates to the use of 7-hydroxymatairesinol and a composition thereof for ameliorating the neurodegenerative disorders, in particular the disorders associated with dopaminergic neurons loss, such as the Parkinson's disease.

BACKGROUND OF THE INVENTION

Neurodegeneration is the progressive loss of structure or function of neurons, including death of neurons. Many neurodegenerative diseases, such as amyotrophic lateral sclerosis, Parkinson's disease, Alzheimer's disease, and Huntington's disease, occur as a result of neurodegenerative processes and are incurable, resulting in progressive degeneration and/or death of neuron cells.

Degeneration of dopaminergic neurons results in the depletion of the dopamine neurotransmitter production, which manifests clinically as motor dysfunctions. Parkinson's disease, the prototype of movement disorders, is characterized by the progressive loss of dopaminergic neurons in the substantia nigra pars compacta (SNc) and consequent dopaminergic denervation of the corpus striatum, the main recipient of SNc neuron projections.

Typical Parkinson's disease motor symptoms include resting tremor, bradykinesia, rigidity, and postural instability, and tend to appear as the SNc cell loss exceeds 50-60%. Parkinson's disease clinical manifestations also include non-motor symptoms, such as autonomic and gastrointestinal dysfunctions, sleep disorders, cognitive deficits and depression.

Age is the main risk factor for Parkinson's disease, prevalence being 1-2% at 65 years and raising to 3-5% at the age of 85. Women show a lower risk of developing the disease and their age of onset tends to be higher with respect to men. These differences have been attributed to sex steroid hormones, oestrogens in particular, which may exert neuroprotective effects on nigrostriatal neurons.

Several mechanisms involved in Parkinson's disease pathogenesis are known in the art, including neuroinflammation and oxidative stress. Neuroinflammation is primarily driven by the activation of microglia, the resident macrophage population of the central nervous system. Activated microglia can be polarized toward two different phenotypes, M1 (cytotoxic) or M2 (cytoprotective), depending on the modulatory effects of molecules released into extracellular space and, consequently, on the microenvironment shared with neurons. The balance between the two phenotypes determines the impact of microglia activation on the neurodegenerative process.

Oxidative stress can also contribute to dopaminergic degeneration in Parkinson's disease, since the disruption of the redox potential in neurons interferes with several biological processes, ultimately leading to cell death. The SNc is typically exposed to high rates of reactive oxygen species (ROS) formation, due to dopamine auto-oxidation and the high iron content that characterizes SNc neurons, which further accelerates ROS formation.

Considering their crucial roles, both neuroinflammation and oxidative stress may therefore represent key therapeutic targets for Parkinson's disease.

Pharmacological treatments for Parkinson's disease known in the art are mainly symptomatic and directed at compensating its characteristic loss of dopamine. The main used drug, L-3,4-dihydroxyphenylalanine (L-dopa), considerably improves motor symptoms. L-Dopa prolonged use, however, is hampered by side effects, termed "motor complications", mainly represented by involuntary movements (dyskinesia) and profound fluctuations ("on/off" state) in the motor response to the drug.

The development of pharmacological treatments that may modify the disease's progression is currently the main priority in the Parkinson's disease field. Research attempts, in this context, have frequently considered the use of natural products, such as plant extracts and their secondary metabolites, as potential therapeutics with neuroprotective activity.

Several works can be found in the literature describing the protective effect of natural and endogenous antioxidants, such as polyphenols, against oxidative stress in experimental Parkinson's disease models, both in vitro and in vivo (Sutachan J. J., et al., *Cellular and molecular mechanisms of antioxidants in Parkinson's disease*, Nutritional Neuroscience 2012, 15(3), 120-126).

It has also been shown that polyphenols can modulate the neuroinflammatory process by inhibiting the expression of inflammatory genes (Aquilano K., et al., *Role of nitric oxide synthases in Parkinson's disease: a review on the antioxidant and anti-inflammatory activity of polyphenols*, Neurochemistry Research 2008, 33 (12), 2416-2426).

In particular lignans, a class of polyphenols acting as phytoestrogens, possess considerable biological properties that may be exploited if cytoprotection must be achieved.

Lignans are natural compounds commonly found in whole grains, seeds, nuts, legumes and vegetables. They are expected to have beneficial effects in humans after fermentative conversion in the colon, producing enterolactone and enterodiol. Indications that lignans could be characterised as antioxidants, phytoestrogens and modulators of nuclear receptors have also been obtained through a few mechanistic studies.

7-hydroxymatairesinol (HMR), sold under the trademark HMRlignan™ (Linnea S A, Riazzino, Switzerland), is the main single component of lignans in Norway spruce (*Picea abies*), reaching a concentration of about 60 percent of total lignans, which occurs mainly in unconjugated free form.

Lignans concentration in thick roots, mainly represented by HMR, is 2-3 percent. Abundance of lignans, mainly represented by HMR, occur in the heartwood of branches (5-10 percent) and twists, especially in the knots, where the amount of lignans, mainly represented by HMR, may be higher than 10 percent. These concentrations are about hundred-fold compared to ground flaxseeds powder known as lignan-rich material, mainly represented by lignan secoisolariciresinol diglucoside (SDG).

HMR is generally metabolized by intestinal bacteria to the mammalian lignan enterolactone and is provided with immunomodulatory, anti-inflammatory and anti-apoptotic effects, possibly mediated by its interaction with oestrogen receptor E2 (Cosentino M., et al., *Immunomodulatory activity of the lignan 7-hydroxymatairesinol potassium acetate (HMR/lignan) extracted from the heartwood of Norway* spruce (*Picea abies*), Int. Immunopharmacol. 2010, 10 (3), 339-343; Cosentino M., et al., *Estrogenic activity of 7-hydroxymatairesinol potassium acetate (HMR/lignan™) from Norway spruce (Picea abies) knots and of its active metabolite enterolactone in MCF-7 cells*, Pharmacological Research, 2007, 56, 140-147; Spilioti E., et al., *Lignans 7-hydroxymatairesinol and 7-hydroxymatairesinol 2 exhibit anti-inflammatory activity in human aortic endothelial cells*, Mol Nutr. Food Res. 2013).

WO2006/072647 discloses the use of HMR for preventing or alleviating the symptoms relating to oestrogen deficiency in an individual, such as menopausal or postmenopausal symptoms, climacteric symptoms, hot flushes, vaginal dryness, vaginal atrophy, atrophy of the lower urinary tract, loss of bone mineral content, menopausal vasomotor symptoms, mood swings, insomnia, osteoporosis or any other menopause associated condition.

Antioxidant and antitumoral properties have also been proposed for HMR.

U.S. Pat. No. 6,451,849 discloses the use of HMR for prevention of cancers, certain non-cancer, hormone dependent diseases and/or cardiovascular diseases. The publication also indicates that HMR can be effective as such due to its antioxidative activity in vitro.

WO2015/173345 discloses the use of HMR for preventing, alleviating or treating the metabolic syndrome conditions, such as visceral obesity, steatosis, inflammation, dyslipidaemia, insulin sensitivity and high blood glucose.

Animal models able to investigate the pathogenesis and pathophysiology of Parkinson's disease are well known in the art.

These models have been classically based on the systemic or local (intracerebral) administration of neurotoxins that are able to replicate most of the pathological and phenotypic features of Parkinson's disease in mammals.

The prototypical model based on local injection of a neurotoxin is the 6-hydroxydopamine (6-OHDA) model, which was also the first Parkinson's disease animal model ever generated.

6-OHDA can be injected into the striatum, inducing prompt damage of striatal terminals, followed by delayed, progressive cell loss of SNc neurons, which are secondarily affected through a 'dying back' mechanism. The degree of SNc damage obtained with this procedure is of around 50-70%, and evolves over a period of 4-6 weeks. This provides a progressive model of nigrostriatal degeneration, similar to the gradual evolution of the neurodegenerative process of human Parkinson's disease (Blandini F., et al., *Animal models of Parkinson's disease*, Federation of European Biochemical Societies Journal 2012, 279 (7), 1156-1166).

SUMMARY OF THE INVENTION

The Applicant faced the problem of selecting an active compound able to alleviating or treating the neurodegenerative disorders, such as the diseases associated with dopaminergic neurons loss.

In particular, the Applicant faced the problem of selecting an active compound able to alleviating or treating Parkinson's disease.

The Applicant surprisingly found that 7-hydroxymatairesinol (HMR) was able to reduce the nigrostriatal damage, characterised by dopaminergic terminals and neurons loss, linked to Parkinson's disease.

The Applicant also surprisingly found that HMR was able to reduce the microglia activation linked to Parkinson's disease.

Finally, the Applicant unexpectedly found that HMR was also able to reduce the microglia polarization toward the M1 (cytotoxic) phenotype, favouring the expression of the M2 (cytoprotective) phenotype.

The obtained results can also be considered promising in reducing neurodegeneration of other areas of the brain and/or the central nervous system, as one of the most striking hallmarks shared by various neurodegenerative diseases, including Parkinson's disease, Alzheimer's disease (AD), and amyotrophic lateral sclerosis, is microglia-mediated neuroinflammation (Tang Y et al., Differential Roles of M1 and M2 Microglia in Neurodegenerative Diseases, Mol Neurobiol. 2016 March; 53(2):1181-94. doi: 10.1007/s12035-014-9070-5. Epub 2015 Jan. 20).

Accordingly, a first aspect of the present invention relates to the use of 7-hydroxymatairesinol (HMR) for alleviating or treating the neurodegenerative disorders.

More in particular, the present invention relates to the use of HMR for alleviating or treating the disorders associated with dopaminergic neurons loss, such as the Parkinson's disease.

A second aspect of the present invention relates to a composition, such as a pharmaceutical composition or a food product, comprising HMR, together with one or more additional ingredient and/or excipient, for alleviating or treating the neurodegenerative disorders, and particularly for alleviating or treating the disorders associated with dopaminergic neurons loss, such as the Parkinson's disease.

A third aspect of the present invention relates to a method for alleviating or treating the neurodegenerative disorders, and particularly for alleviating or treating the disorders associated with dopaminergic neurons loss, such as the Parkinson's disease, in a person in need thereof comprising administering to said person an effective amount of HMR.

DETAILED DESCRIPTION OF THE INVENTION

This invention relates to the use of 7-hydroxymatairesinol (HMR) for alleviating or treating the disorders associated with dopaminergic neurons loss.

More in particular, the invention relates to the use of HMR for alleviating or treating Parkinson's disease.

The chemical structure of HMR is represented by the following formula (I).

HMR is a lignan, i.e., a group of chemical compounds found in plants derived from phenylalanine via dimerization of substituted cinnamic alcohols, known as monolignols, to a dibenzylbutane skeleton. Lignans are one of the major classes of phytoestrogens, which are oestrogen-like chemicals and also act as antioxidants.

Flax seeds and sesame seeds contain higher levels of lignans than most other foods. Considerable amounts of lignans are also found in coniferous trees. The type of lignans differs in different species and the amounts of lignans vary in different parts of the trees.

HMR is the far most abundant single component of lignans in spruce (*Picea abies*) extracts, wherein reaches a concentration of about 60% w/w of total lignans.

In spruce, lignan concentration in thick roots is 2-3 percent. Abundance of lignans occurs in the heart wood of branches (5-10 percent) and twists, especially in the knots, where the amount of lignans may be higher than 10 percent. These concentrations are about hundred-fold compared to ground flaxseeds powder known as lignan-rich material.

Isolation of HMR for use in this invention can be made from oversize chip fraction (containing branches, twists and knots) of compression wood of spruce (*Picea abies*). Total extract of *Picea abies* (TEP, containing HMR and the isomer) and HMRlignan™ purified HMR (containing mainly HMR) are commercially available from Linnea SA, Riazzino, Switzerland.

The neurodegenerative disorders that can be alleviated or treated according to the present invention are those related to microglia mediated neuro-inflammation, such as amyotrophic lateral sclerosis, Parkinson's disease, and Alzheimer's disease.

More in particular, the present invention is useful in reducing the nigrostriatal damage, characterised by dopaminergic terminals and neurons loss, linked to Parkinson's disease.

This invention also relates to a composition, such as a pharmaceutical composition or a food product, comprising HMR, together with one or more additional ingredient and/or excipient for alleviating or treating the disorders associated with dopaminergic neurons loss, in particular Parkinson's disease.

The pharmaceutical composition according to this invention is preferably an oral or buccal formulation, but other form of administration can be envisaged, such as, for example, parenteral formulation, suppository formulation, topical formulation, and the like.

The required amount of the active compound (HMR) will vary with the particular condition to be treated. A typical dose of HMR ranges from about 10 to about 500 mg per day and adult person, preferably from about 30 to about 300 mg per day and adult person.

Preferably, the form of the composition of the present invention may be represented by a form which is useful for the oral or buccal administration, such as for example solution, suspension, syrup, gel, tablets, granules, pellets, capsules, lozenges, pills, and spray. Other forms of composition can be envisaged for different administration routes.

The food product according to this invention can be any edible, non-toxic solid or liquid product suitable to be admixed with HMR without affecting the properties of HMR. The role of the product is mainly to make the exact dosage of HMR easier. A suitable concentration is for example 100 mg to 1 g of HMR per 100 g of enriched product.

The food product according to this invention is especially a functional food, a nutritional supplement, a nutraceutical, and a health food. A suitable concentration of HMR in the food product is, for example, 1 to 20 mg of HMR per 100 g of food product.

The additional ingredient and/or excipient of the pharmaceutical composition of the present invention can be any pharmaceutically acceptable ingredient and/or excipient.

The term pharmaceutically acceptable excipient is understood to comprise without any particular limitations any material which is suitable for the preparation of a pharmaceutical composition which is to be administered to a living being. As already discussed, depending upon the role performed, excipients are classified into (i) filler excipients, (ii) production excipients, (iii) preservative excipients, and (iv) presentation excipients. These materials, which are known in the art, are for example (i) diluents, absorbents, adsorbents, fillers and humectants, (ii) lubricants, binders, glidants, plasticisers and viscosity modifiers, (iii) preservatives, antimicrobials, antioxidants and chelating agents, and (iv) flavourings, sweeteners and colouring agents.

The additional ingredient and/or excipient of the food product of the present invention can be any edible ingredient and/or excipient.

Advantageously, the food product of the present invention comprises at least one edible ingredient selected from the group comprising carbohydrates, proteins, amino acids and derivatives, lipids, phospholipids, vitamins and mineral salts.

The food product of the present invention may be in the form of a food supplement.

A food supplement contains only some of the nutritional substances required to satisfy the user's daily requirements in terms of proteins and energy intake. Thus the formulation will be capable of providing less than 1500 kcal, preferably from 1 to 1000 kcal per day. Again in this case the formulation may be in solid or liquid form as described above, for addition to normal diet or as a component of normal diet.

The food product of the present invention may contain further conventional food additives to improve its appearance, pleasantness and preservation, such as for example colouring agents, preservatives, antioxidants, acidity regulators, thickeners, stabilisers, emulsifiers, flavour enhancers, flavourings, humectants and sweeteners.

BRIEF DESCRIPTION OF THE DRAWINGS

The present invention will be better understood by reading the following examples, given by way of illustration and not of limitation, to be read with the accompanying drawings, wherein.

EXAMPLES

The effects of natural compound HMR were tested in a rodent model of Parkinson's disease-like nigrostriatal neurodegeneration caused by stereotaxic injection of dopaminergic neurotoxin 6-OHDA.

The experiments were carried out on male Sprague-Dawley rats (Charles River, Calco, LC, Italy), weighing 200-225 g at the beginning of the experiment, housed one per cage at 20-22° C. on a 12-h light/dark cycle, with food and water ad libitum. Animals were left in the housing facilities for at least 1 week before initiating the experiments.

The Parkinson's animal model used in the present experimental protocol is based on the local, unilateral injection of the 6-hydroxydopamine (6-OHDA) neurotoxin into the corpus striatum via stereotactic surgery.

Animals were anaesthetized with Zoletil (50 mg/kg; Virbac) and placed into a stereotactic frame (Stoelting), with the incisor bar positioned 3.3 mm below the interaural line. Animals received a unilateral injection of 6-OHDA (20 μg in 3 μL of saline solution with 0.02% ascorbic acid; Sigma) into the right striatum (1.0 mm anterior, 3.0 mm lateral and 5.0 mm ventral, with respect to bregma and dura) at 1 μL/min using a Hamilton 10 μL syringe with a 26-gauge needle. The needle was left in place for 5 min before being retracted to allow complete diffusion of the medium, and wounds were clipped.

Rats (n=33) were randomly assigned to different treatment groups, in order to evaluate the effects of HMR when this was administered before (PRE group) or after (POST group) induction of the nigrostriatal lesion.

Animals in the PRE group received for 4 weeks before 6-OHDA infusion either 5% sucrose enriched food with HMR (10 mg/Kg per day; n=9) or 5% sucrose enriched food without HMR (vehicle; control n=8). After 4 weeks the animals were subjected to 6-OHDA injection and sacrificed after 4 more weeks.

Animals in the POST group received 5% sucrose enriched food with HMR (10 mg/Kg per day; n=8) or vehicle (control, n=8) for 4 weeks, starting right after the 6-OHDA injection. The animals were sacrificed at the end of the fourth week of treatment.

Food consumption and body weight changes were monitored daily. No differences between treated and untreated rats were detected, either in food intake or weight gain, throughout the experiments, indicating that all animals in the active treatment group received the same amount of HMR.

Twenty-eight days after 6-OHDA infusion, animals were deeply anesthetized with 150 mg/kg of Zoletil, underwent cardiac puncture blood sampling and were perfused with saline and ice-cold 4% paraformaldehyde (Merck).

Brains were rapidly removed, post-fixed for 24 hours in the same fixative and subsequently transferred in solutions of sucrose at increasing concentrations (up to 30%).

Brains were cut in serial coronal sections containing both the striatum and the SNc using a microtome (Leica SM 2000R) and were stained for different markers.

Different tests were run on blood and brain samples.

Statistical analysis results were expressed as mean±SEM (Standard Error of the Mean). Statistical analysis was performed using the GraphPad Prism 3 software (GraphPad software, SanDiego, Calif., USA). Comparisons between groups were made using Student's t-test for unpaired data. Statistical significance was set at $p<0.05$.

Image analysis was performed using an AxioSkop2 microscope connected to a computerized image analysis system (AxioCam MR5) with dedicated software (AxioVision Rel 4.2).

Extensive experimental data, shown in the following examples 1 to 5, demonstrated that chronic treatment with HMR, when started right after the infusion of 6-OHDA, induces an appreciable reduction of the nigrostriatal damage caused by the neurotoxin. This was associated with reduced microglia activation and a preferential expression of the anti-inflammatory, cytoprotective M2 microglial phenotype. No such effect was observed in animals treated with HMR before 6-OHDA injection.

Test 1—HMR Plasma Levels Assay

Concentration of HMR and its major metabolite enterolactone was measured in plasma samples (50 μL) from rats fed for 4 weeks with 5% sucrose enriched food with HMR, using an LC-MS/MS system (AP14500 Qtrap ABSciex).

Calibration curves in the range from 0.1 ng/mL to 100 ng/mL were obtained from measurements on control samples containing the pure analytes, prepared from stock solutions of HMR and enterolactone in MeOH at the concentration of 1 mg/mL. Said stock solutions were diluted in acetonitrile (ACN) at a concentration of 250 μg/mL, then working solutions were prepared by sequential dilution in ACN.

45 μL of plasma and 5 μL of working solution were added to 300 μL of an ACN solution containing the internal standard catechin (conc. 200 ng/mL). After mixing, samples were centrifuged for 5 min at 3000 g at 5° C., and injected into LC-MS/MS.

The plasma samples from the in vivo treatment were prepared subjecting 50 μl of sample to centrifugation for 5 min at 3000 g at 5° C., and were injected into LC-MS/MS.

Calibration curves allowed determining, by comparison, the amount of each analytes in the plasma samples obtained from the rats of the study.

HMR was detected in the plasma of all animals in the active treatment groups, with a mean value of 0.92±0.74 ng/mL.

Enterolactone was below the detection limit of 0.1 ng/mL (no peak detected) in all the analysed samples.

Test 2—Nigrostriatal Damage Evaluation

The nigrostriatal lesion was assessed by immunohistochemistry for the dopaminergic marker tyrosine hydroxylase (TH) on coronal sections of both SNc and striatum.

Sections were processed with rabbit anti-TH primary antibody (1:1000, Chemicon) and a biotinylated anti-rabbit IgG secondary antibody (Vector Laboratories), then revealed using a commercial kit based on the avidin-biotin technique (Vectastain ABC Elite kit, Vector Laboratories). Reaction products were developed using nickel-intensified 3'-3'-di-aminobenzedine tetra-hydrochloride (DAB Substrate Kit for Peroxidase, Vector Laboratories).

In the SNc, TH-positive (TH+) neurons were counted bilaterally on every four section throughout the entire nucleus using the unbiased stereological optical fractionator method (Stereo Investigator System, Microbrightfield Inc.).

TH+ neurons are those still producing dopamine, therefore the extent of the neurodegeneration, represented by the amount of dead dopaminergic neurons in the lesioned hemisphere, was extrapolated by comparison with the amount of active dopaminergic neurons in the intact hemisphere.

Results were expressed as the percentage of TH+ neurons in the lesioned SNc compared to that found in the intact hemisphere, for each group of animals.

On the lesioned striatum, densitometric analysis was performed to evaluate the loss of dopaminergic terminals. In this case, the striatal degeneration was evaluated and expressed as the percentage of striatal volume deprived of TH immunoreactivity, with respect to the entire striatal volume of the lesioned hemisphere.

The intra-striatal injection of 6-OHDA induced marked loss of TH+, dopaminergic, terminals and cell bodies in the ipsilateral nigrostriatal pathway of all vehicle-treated animals; no loss of TH+ terminals or cell bodies was observed in the contralateral, intact, hemisphere.

The comparison between vehicle-treated animals and animals that received HMR before the intra-striatal injection of 6-OHDA showed no differences in nigrostriatal damage, either at the striatal or SNc level.

At day 28 post-surgery, in the lesioned side of the brain it was possible to observe up to 55% TH+ neurons depletion in the SNc and 65% TH+ terminals loss in the striatum, as compared to the contralateral hemisphere, in both HMR-treated and control animals.

Figure 1A:
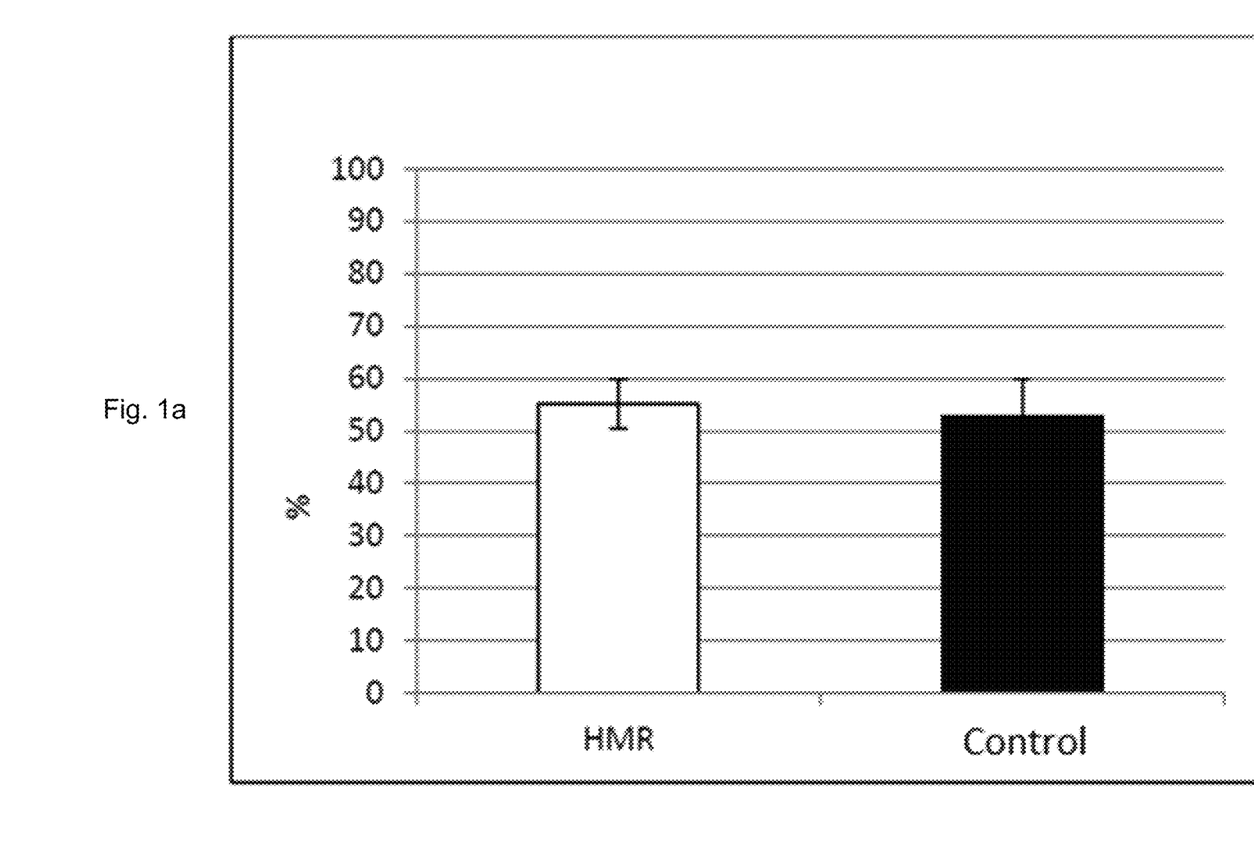
FIGS. 1a and 1b show the comparison of the degeneration expressed as percentage of lesion, in the SNc and striatum respectively, between animals that received HMR before 6-OHDA infusion and vehicle group.
Figure 1B:
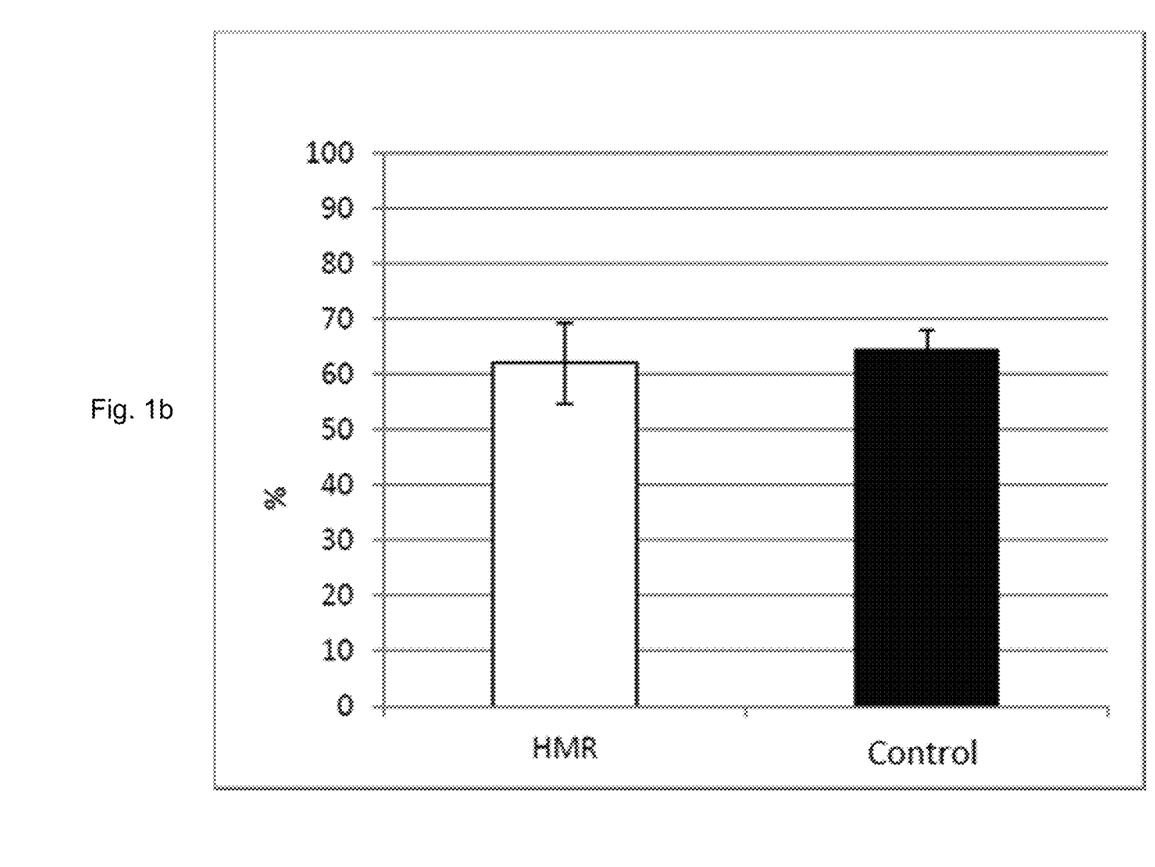

FIGS. 1a and 1b show the comparison of the degeneration expressed as percentage of lesion, in the SNc and striatum respectively, between HMR-treated and vehicle-treated animals.

Surprisingly, substantial differences were evident between animals that received HMR immediately after 6-OHDA infusion and the control group.

At day 28 post-surgery, in the lesioned SNc it was possible to observe about 20% reduction of the 6-OHDA induced loss of TH+ neurons in rats treated with HMR after 6-OHDA injection, as compared to the vehicle-treated animals (p=0.055).

Additionally, in the lesioned hemisphere striatum a statistically significant (p<0.05), about 32% reduction of TH+ terminal loss was observed in rats treated with HMR, as compared to the control group.

Figure 2A:
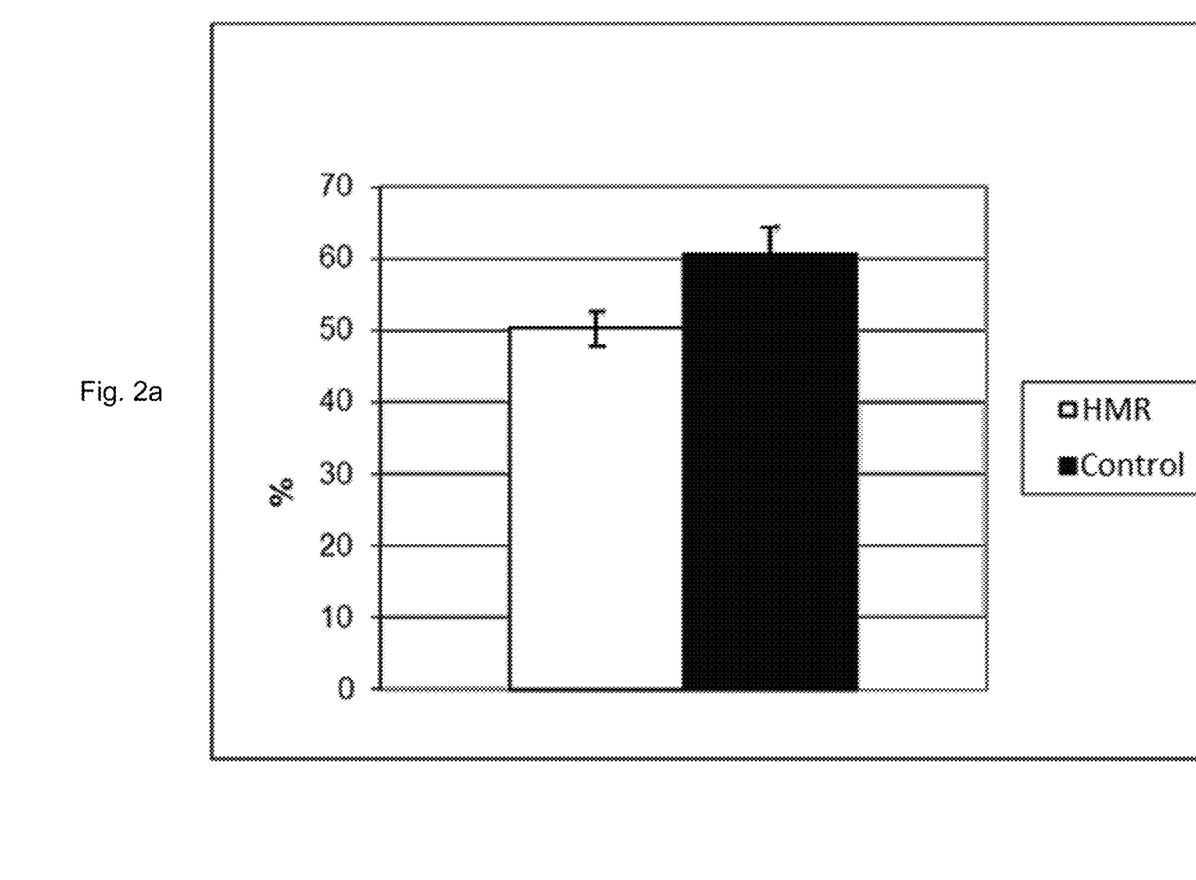
FIGS. 2a and 2b show the comparison of the degeneration expressed as percentage of lesion, in the SNc and striatum respectively, between animals treated with HMR after the 6-OHDA injection and the control group.
Figure 2B:
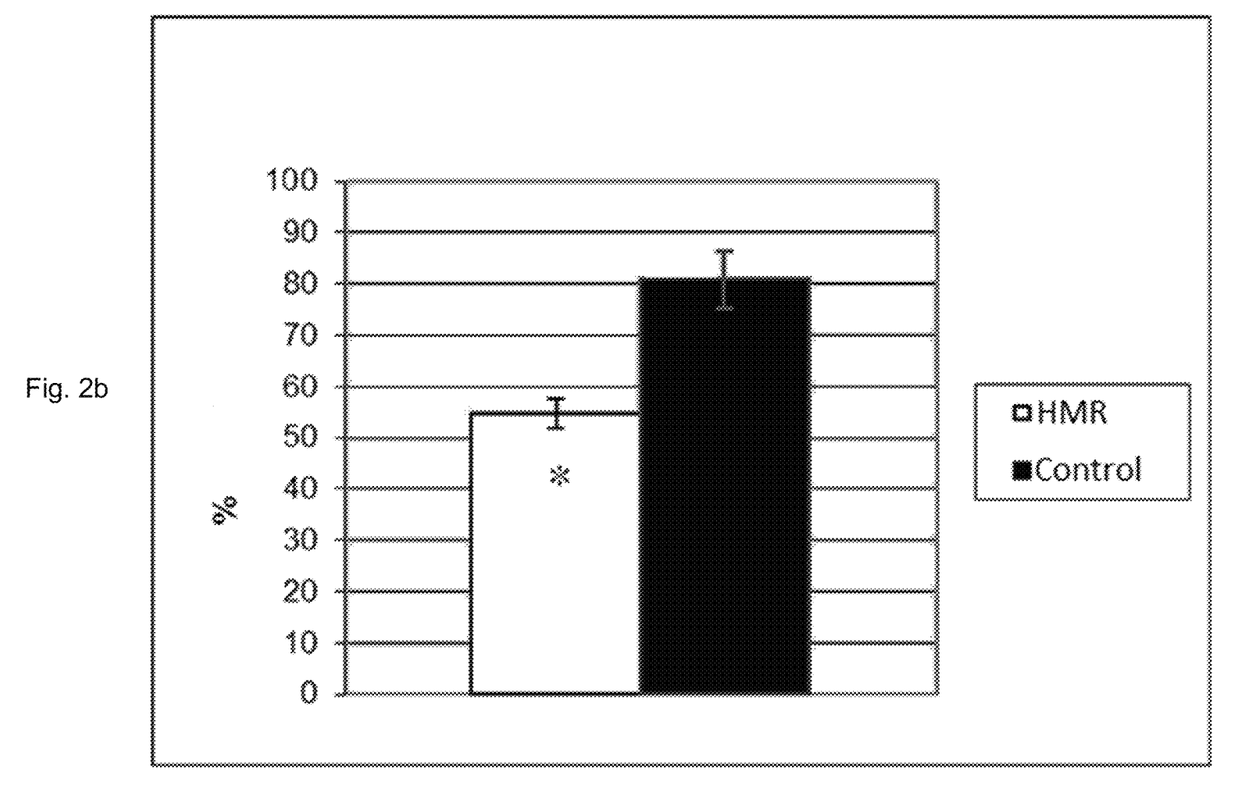

FIGS. 2a and 2b show the comparison of the degeneration expressed as percentage of lesion, in the SNc and striatum respectively, between animals treated with HMR after the 6-OHDA injection and the control group.

Figure 3A:
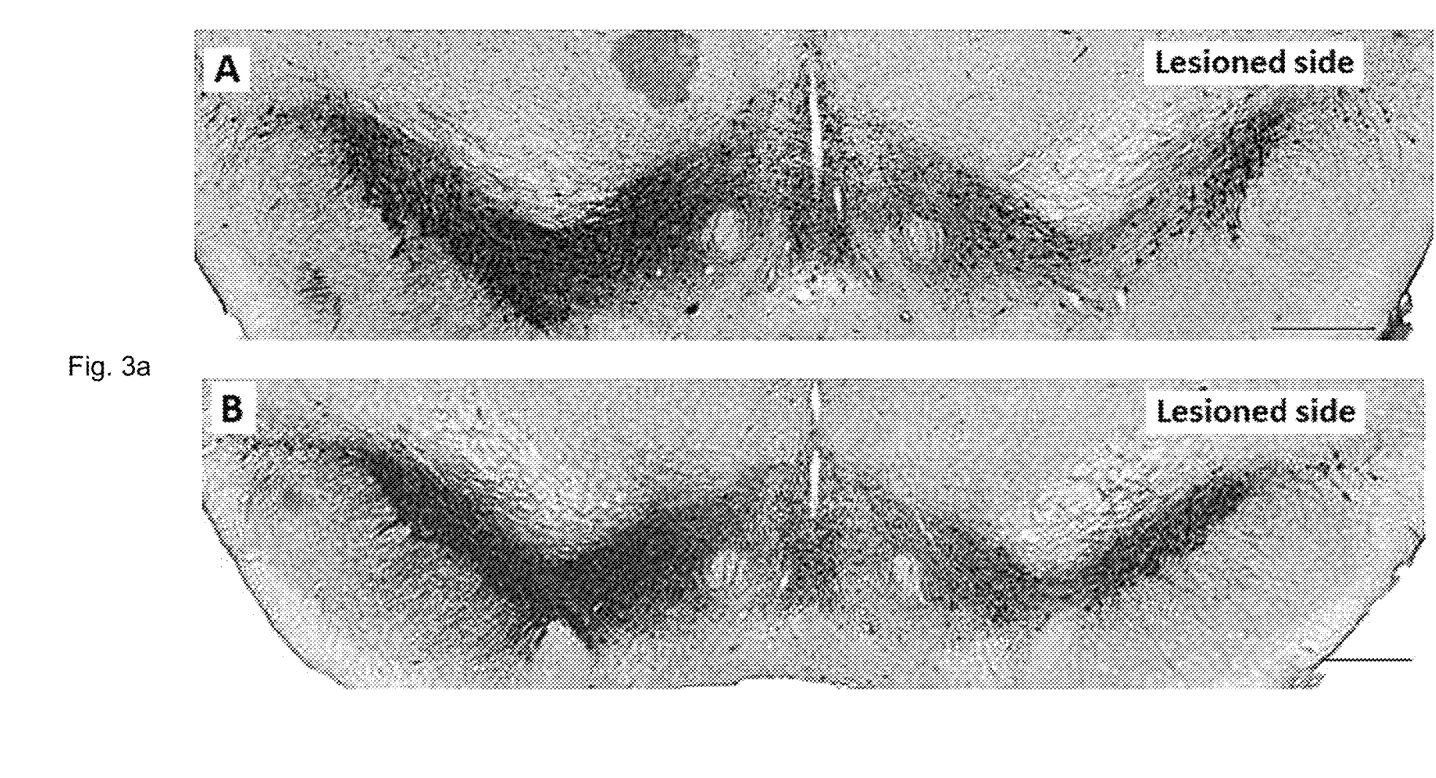
FIGS. 3a and 3b show the comparison of representative images of the damage (TH+ tissue in black), in the SNc and striatum respectively, between vehicle-treated (image A) and animals treated with HMR after infusion with 6-OHDA (image B).
Figure 3B:
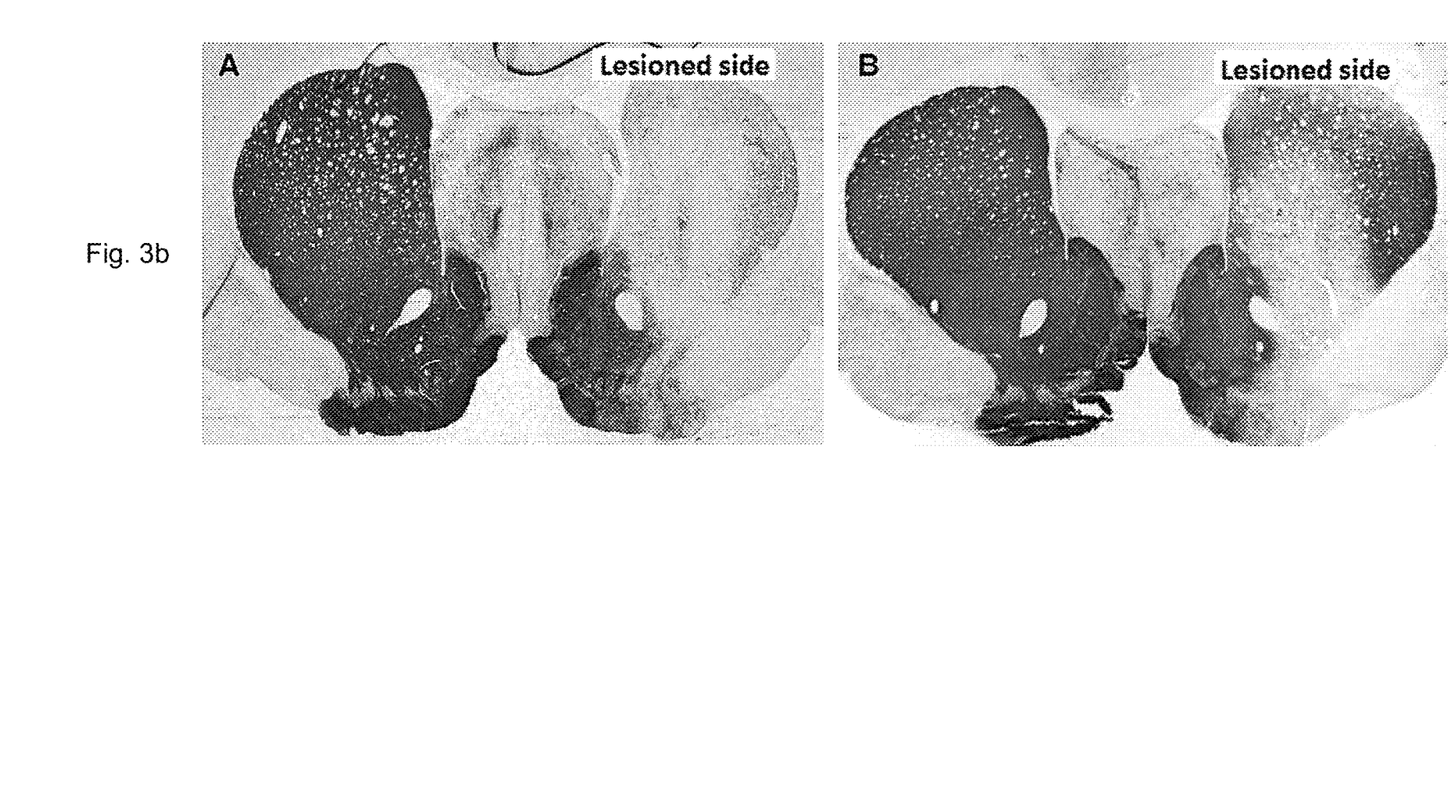

FIGS. 3a and 3b show the comparison of representative images of the damage, in the SNc and striatum respectively, between vehicle-treated (image A) and HMR-treated (image B) animals. In both cases it is possible to appreciate the difference between the TH+ tissue (black) and the lesion (grey).

Test 3—Neuroinflammation Evaluation Through Microglia Activation Assessment.

The evaluation of the 6-OHDA induced neuroinflammation was carried out via immunofluorescent staining of coronal SNc sections of both HMR-treated and control animals.

Microglia activation was assessed by observing sections of the lesioned SNc stained for CD11 b, under low and medium magnification (20×-40×), both quantitatively, by counting the microglial cells in the lesioned SNc, and qualitatively, analysing the morphological changes of the cells.

Mouse anti CD11b (MCA275R, Serotec, 1:300) primary antibody was used to assess microglia activation and density in the SNc. Anti-TH primary antibody was added for localization and cell count. Goat anti-mouse AlexaFluor488 and goat anti-rabbit AlexaFluor594 (Life Sciences, 1:300) were used as secondary antibodies.

Cell count was performed by analysing three different SNc sections, chosen according to rostro-caudal coordinates.

Morphological changes mirroring the state of activation were scored according to the Colburn scale. Cell density was assessed by counting CD11 b+ cells from a stack of 16 pictures (in a 0.04 mm$^2$ frame, 1 µm-thick, 40× magnification) taken from three discrete areas of the same SNc section.

Colburn's scale takes into account four activation stages, which differ for the cells morphology and density, and are summarized below.

Resting stage (score 0): microglial cells are ramified, well spaced-out, with a small cell body.

Stage 1 (score +): microglial cells are ramified, with a decreased intercellular space.

Stage 2 (score ++): microglial cells show a loss of ramification and increased density.

Stage 3 (score +++): microglial cells show short and think ramifications.

Figure 4:
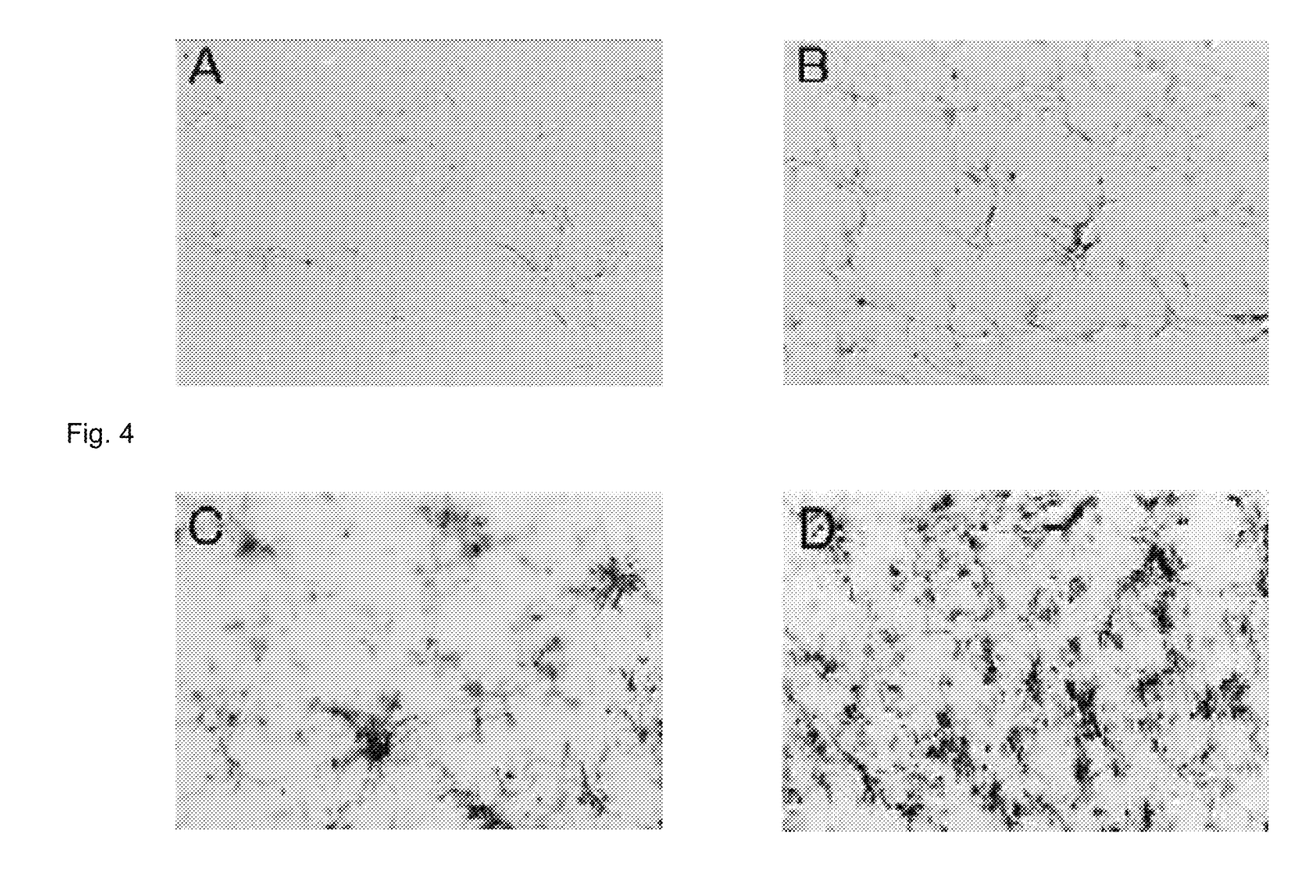
FIG. 4 shows representative images for activation stages 1 to 4 of the Colburn's scale.

FIG. 4 shows representative images for each activation stage of the Colburn's scale.

Figure 5:
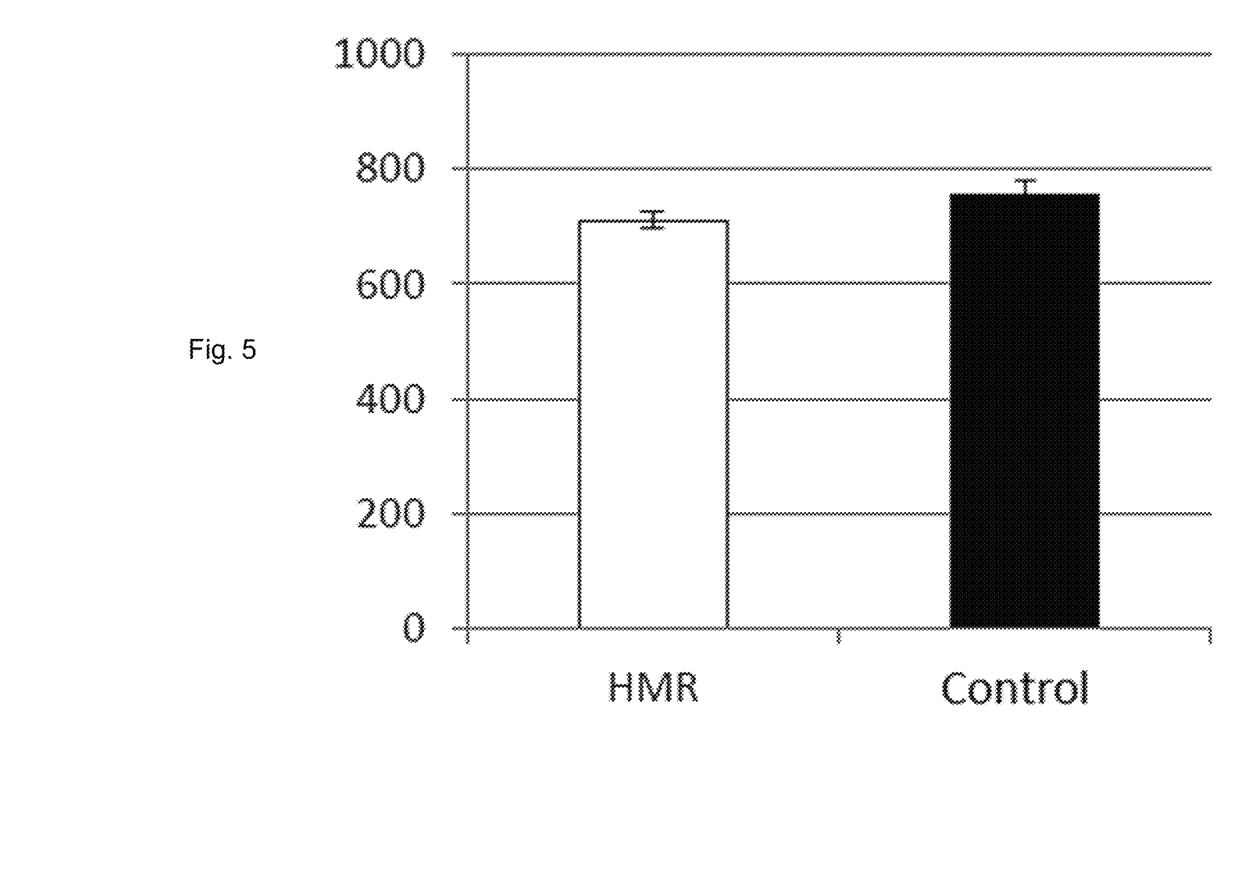
FIG. 5 shows the comparison of the number of CD11b+ cells per $mm^2$ of SNc in both vehicle-treated and HMR-treated animals of the PRE-group.

The comparison between vehicle-treated animals and animals that received HMR before the intra-striatal injection of 6-OHDA showed no differences in the microglial cell count. Both groups showed an average of 750 cells/mm$^2$. FIG. 5 shows the comparison of the number of CD11b+ cells per mm$^2$ of SNc in both vehicle-treated and HMR-treated animals of the PRE-group.

Morphological evaluation showed moderate microglia activation in both vehicle-treated and HMR-treated animals, but no differences were observed in the density of CD11b+ cells between the two groups. The below table 1 summarizes the morphological evaluation of both groups according to Colburn's scale.

TABLE 1

| Animals | Colburn's score |
|---|---|
| HMR-treated PRE-group | ++ |
| Control group | ++ |

Surprisingly, animals that received HMR immediately after 6-OHDA infusion showed lower microglia activation than the control group, both in terms of cell count and of morphology.

Table 2 below summarizes the morphological evaluation of both groups according to Colburn's scale.

TABLE 2

| Animals | Colburn's score |
|---|---|
| HMR-treated POST-group | + |
| Control group | ++ |

Figure 6:
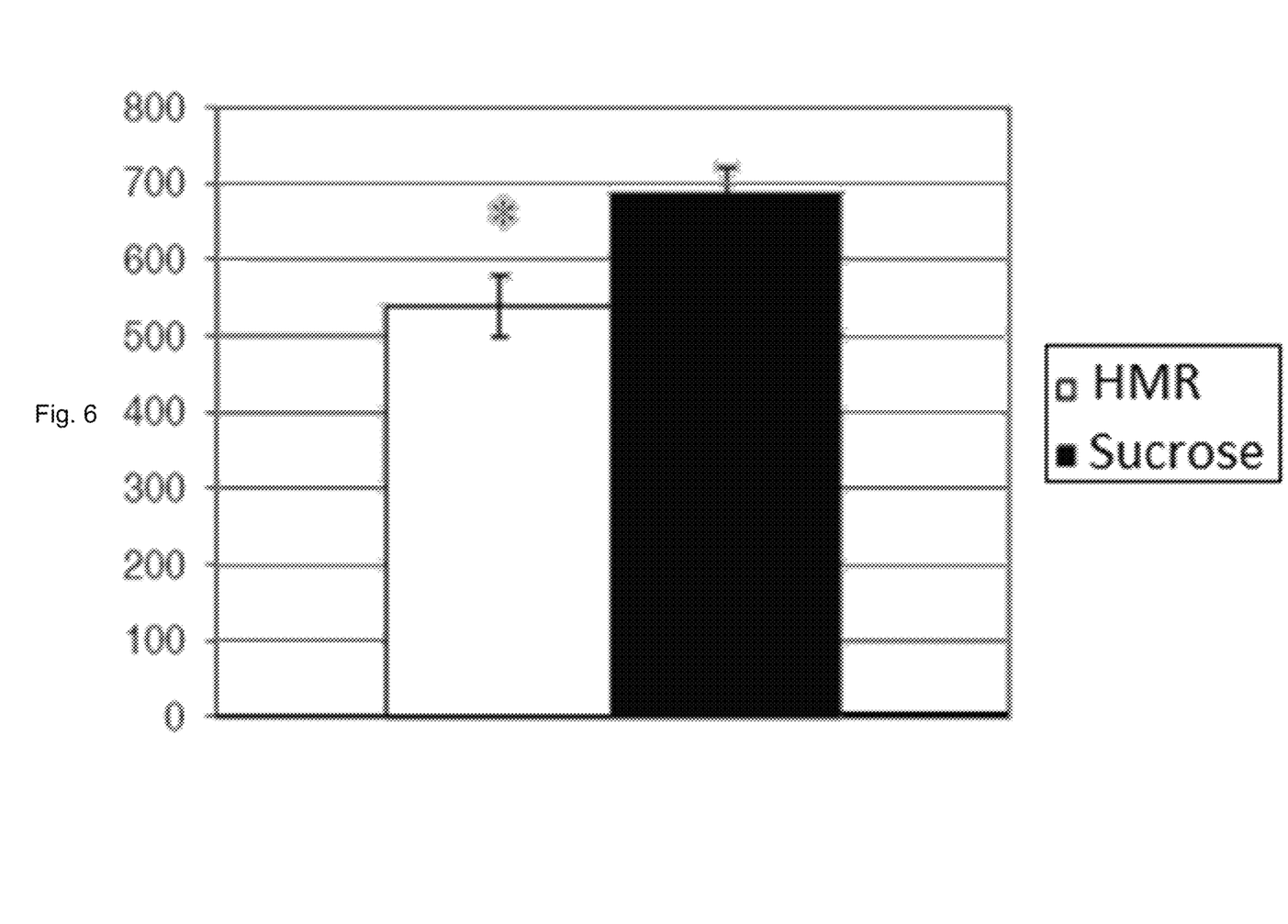
FIG. 6 shows the comparison of the number of CD11b+ cells per mm² of SNc in both vehicle-treated and HMR-treated animals of the POST-group.

This was accompanied by a significant decrease in the density of CD11 b+ cells in the SNc of HMR-treated animals (550 cells/mm$^2$) with respect to the vehicle-treated group (750 cells/mm$^2$). FIG. 6 shows the comparison of the number of CD11b+ cells per mm$^2$ of SNc in both vehicle-treated and HMR-treated animals of the POST-group.

Test 4—Analysis of Microglia Polarization.

The analysis of microglia polarization was performed by evaluating the percentage of CD32+ and CD206+ cells, respectively M1 and M2 phenotypes marker, of the total microglia cells in the lesioned SNc, using respectively CD32 or CD206 (Santa Cruz, 1:300) antibodies.

Since no significant differences in microglial activation were observed between vehicle-treated animals and animals that received HMR before the intra-striatal injection of 6-OHDA, microglia polarization was evaluated only in the groups treated with HMR after 6-OHDA infusion.

Remarkably different patterns of microglia polarization were observed in the HMR-treated animals as compared to the control group.

Microglia polarization was mainly oriented toward the neuroprotective, M2 (CD11b+/CD206+) phenotype in animals treated with HMR, while vehicle-treated animals showed that microglia was mainly polarized toward the M1, neurotoxic (CD11b+/CD32+) phenotype. No evidence of the M2 phenotype was detected in this latter group.

Test 5—Oxidative Stress Evaluation

Plasma levels of reduced (GSH) and oxidized (GSSG) glutathione were estimated by using a biochemical Glutathione assay kit (Cayman Chemical), as an index of antioxidant effect of HMR treatment.

Results were expressed as a GSH/GSSG ratio.

Since no significant difference in neuroinflammation was observed between vehicle-treated animals and animals that received HMR before the intra-striatal injection of 6-OHDA, oxidative stress was evaluated only in the groups treated with HMR after 6-OHDA infusion.

In animals treated with HMR after 6-OHDA infusion, the results, although not reaching statistical significance, showed a trend toward an increased GSH/GSSG ratio, when compared to vehicle-treated animals, expressing greater availability of reduced GSH.

Figure 7:
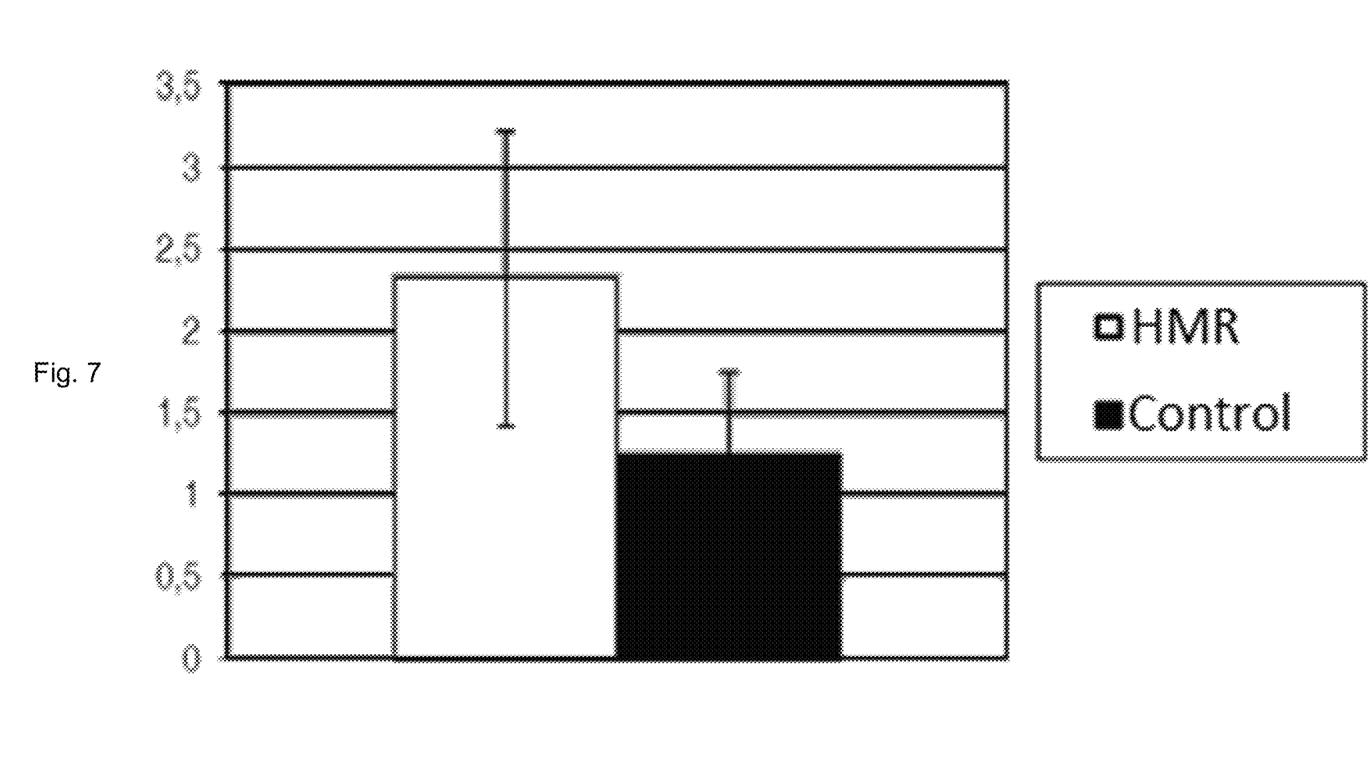
FIG. 7 shows GSH/GSSG ratio in both vehicle-treated and HMR-treated animals of the POST-group.

FIG. 7 shows GSH/GSSG ratio in both vehicle-treated and HMR-treated animals.

The invention claimed is:

1. A method for alleviating Parkinson's disease in a person in need thereof comprising administering to said person an effective amount of 7-hydroxymatairesinol (HMR).

2. The method according to claim 1, wherein said effective amount is from about 10 to about 500 mg per day per adult person.

3. The method according to claim 1, wherein said effective amount is from about 30 to about 300 mg per day per adult person.

* * * * *